United States Patent
Budolfsen et al.

(10) Patent No.: US 6,232,101 B1
(45) Date of Patent: *May 15, 2001

(54) OXIDASE-PROMOTED GELLING OF PHENOLIC POLYMERS

(75) Inventors: Gitte Budolfsen, Frederiksberg; Hans Peter Heldt-Hansen, Virum, both of (DK)

(73) Assignee: Novozymes A/S Patents, Bagsvaerd (DK)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/732,260

(22) PCT Filed: Jul. 26, 1995

(86) PCT No.: PCT/DK95/00317

§ 371 Date: Oct. 28, 1996

§ 102(e) Date: Oct. 28, 1996

(87) PCT Pub. No.: WO96/03440

PCT Pub. Date: Feb. 8, 1996

(30) Foreign Application Priority Data

Jul. 26, 1994 (DK) .................................................. 0882/94

(51) Int. Cl.$^7$ .............................. C12P 19/00; C12P 19/04
(52) U.S. Cl. .............................. 435/72; 435/101; 435/99; 435/274; 435/275; 536/123.1; 536/126; 536/128; 514/54; 424/488

(58) Field of Search ................................. 435/72, 99, 101, 435/274, 275; 536/123.1, 126, 128; 514/54; 424/488

(56) References Cited

U.S. PATENT DOCUMENTS

| 4,672,034 | 6/1987 | Rombouts et al. . |
| 5,346,695 | * 9/1994 | Nonoyama et al. ............... 424/78.08 |

FOREIGN PATENT DOCUMENTS

| 2 261 671 | 5/1993 | (GB) . |
| WO 93/10158 | 5/1993 | (WO) . |
| 9312259 | * 6/1993 | (WO) . |
| WO 96/03440 | 2/1996 | (WO) . |

OTHER PUBLICATIONS

Thibault et al, Carb. Res. 154:205–215 (1986).*
J.F. Thibault et al., "Gelation of Sugar Beet Pectin By Oxidative Coupling", The Chemistry and Technology of Pectin, 1991, pp. 119–133.
Kennedy et al., Elsevier Applied Science, vol. 12, (1990), pp. 353–374.

* cited by examiner

Primary Examiner—Francisco Prats
(74) Attorney, Agent, or Firm—Elias J. Lambiris, Esq.; Jason I. Garbell, Esq.

(57) ABSTRACT

A method for causing gelling or increase of viscosity of an aqueous medium containing a gellable polymeric material having substituents with phenolic hydroxy groups comprises adding an oxidase, particularly a laccase, to the aqueous medium.

21 Claims, No Drawings

US 6,232,101 B1

OXIDASE-PROMOTED GELLING OF PHENOLIC POLYMERS

CROSS-REFERENCE TO RELATED APPLICATIONS

This application is a 35 U.S.C. 371 national application of PCT/DK95/00317 filed Jul. 26, 1995, which is incorporated herein by reference.

FIELD OF THE INVENTION

The present invention relates to a method for causing gelling or increase of viscosity of aqueous media containing gellable polymeric materials having substituents with phenolic hydroxy groups.

BACKGROUND OF THE INVENTION

Certain pectins, e.g. pectin from sugar beets and pectin from spinach, as well as hemicellulosic material from certain cereals, e.g. from wheat and maize, are substituted to some extent with substituents derived from certain carboxylic acids (normally substituted cinnamic acids) containing phenolic hydroxy groups. Substances of this type are, for convenience and brevity, often referred to in the following simply as "phenolic polysaccharides".

A number of naturally occurring phenolic polysaccharides of the above-mentioned type are readily available relatively cheaply and are of proven physiological safety with regard to ingestion by, and contact with, humans and animals. Such phenolic polysaccharides have numerous applications relating to their ability to undergo gelling or viscosity increase under certain conditions. Areas of application of the resulting gelled or viscous products include, but are by no means limited to, the following:

Foodstuff applications: as a thickening and/or stabilising agent in sauces, gravy, desserts, toppings, ice cream and the like; as a setting agent in marmelades, jams, gellies and the like; as a viscosity-regulating agent in flavouring extracts and the like.

Medical/medicinal applications: as a material for drug encapsulation; as a slow release vehicle for drug delivery (e.g. oral, anal or vaginal); as a material for a wound or burn dressing.

Agricultural/horticultural applications: as a slow release vehicle for pesticide delivery (i.e. as a biocontainer); as a plant culture medium.

Oxidative cross-linking of phenolic polysaccharides of plant origin (with resultant gelling) is described in, e.g., FR 2 545 101 and WO 93/10158, and by J. -F. Thibault et al. in *The Chemistry and Technology of Pectin*, Academic Press 1991, Chapter 7, pp. 119–133.

The cross-linking of phenolic polysaccharides may be achieved by purely chemical modification using a powerful oxidant such as, e.g, persulfate [as described in J. -F. Thibault et al. (vide supra) in connection with the gelling of beet pectins].

With respect to enzyme-catalyzed processes, J. -F. Thibault et al. (vide supra) also describe the gelling of beet pectins using a combination of a peroxidase and hydrogen peroxide. Similarly, WO 93/10158 describes gelling of aqueous hemicellulosic material containing phenolic substituents (e.g. substituents derived from "ferulic acid" (i.e. 4-hydroxy-3-methoxycinnamic acid; it does not appear to have been established clearly whether "ferulic acid" embraces cis or trans isomeric forms, or both) using an oxidizing system comprising a peroxide (such as hydrogen peroxide) and an "oxygenase" (preferably a peroxidase).

FR 2 545 101 A1 describes a process for modification (including gelling) of beet pectin involving the use of "an oxidizing system comprising at least an oxidizing agent and an enzyme for which the oxidizing agent in question is a substrate". However, the only types of oxidizing agent and enzyme which are specified and/or for which working examples are given are hydrogen peroxide and peroxidases, respectively.

The documents outlined briefly above describe, inter alia, the use of the resulting modified/gelled materials for medical/medicinal purposes, in cosmetics and/or in foodstuffs. However, neither peroxide treatment nor chemical modification of substances intended for ingestion (e.g. substances for use in foodstuffs) or for uses which may result in more or less prolonged contact with, or close proximity to, skin or mucous membranes are desirable, and such treatments are in fact not permitted in many countries. As will be apparent from the above discussion, there seems to be a lack of real awareness of the possibility of avoiding such undesirable treatments, and it is an object of the present invention to provide an alternative to the existing methods.

SUMMARY OF THE INVENTION

It has now surprisingly been found that gelling or increase in viscosity of aqueous, gellable polymeric materials having substituents with phenolic hydroxy groups, notably phenolic polysaccharides, may be achieved very satisfactorily via the simple addition of an appropriate amount of an enzyme of the oxidase type (vide infra), especially a laccase. Laccases utilize oxygen—very suitably oxygen from the atmosphere—as oxidizing agent, and the use of undesirable reagents such as peroxides may thus be eliminated with the process of the present invention.

Laccases are less powerful oxidation-promotors than, e.g., peroxidases, and it is thus surprising that gelling and/or viscosity increase according to the invention can be achieved in the absence of a powerfully oxidizing peroxide reagent. As mentioned above, laccase-catalyzed oxidation involves oxygen, and the consumption of oxygen in the process of the invention leads to the possibility of exploiting the process in a manner which can be advantageous from the point of view of increasing the shelf-life of, e.g., foodstuffs or medicinal products in the preparation of which the process of the invention is employed, since the consumption of oxygen initially present in a sealed foodstuffs package or the like will reduce the possibility of oxidative degradation of the packaged contents.

DETAILED DESCRIPTION OF THE INVENTION

The present invention thus relates to a method for causing gelling or increase of viscosity of an aqueous medium containing a gellable polymeric material having substituents with phenolic hydroxy groups, the method comprising adding an oxidase, preferably a laccase, to the aqueous medium. As already indicated above, preferred gellable polymeric materials in this connection are phenolic polysaccharides.

Gel Formation

It is believed that the gel formation in aqueous medium occurs as a result of polymerization via cross-linking between the phenolic groups of a polymeric material of the type in question (in the following often referred to simply as a "phenolic polymer"), presumably via the formation of stable phenoxy radicals from the hydroxylated aromatic substituents. Increasing cross-linking in this manner eventually (normally after a period of time varying from a few minutes up to about 24 hours at room temperature) leads to an extended, three-dimensionally cross-linked structure, with attendant gelling.

A given phenolic polymer material of the type in question may, if desired, be copolymerized with other monomeric substances (e.g. simple phenols) or polymeric substances (e.g. simple polyphenols, or other polymeric materials having appropriate phenolic substituents, including certain proteins).

It is well known that the physical properties of gels differ greatly from those of corresponding non-gelled solutions. The physical properties of gelled products, and the properties conferred on a product by inclusion of a gel therein, may be characterized by a variety of techniques.

In one such technique, which is known as "Texture Analysis" and which is employed in the working examples herein (vide infra), the "strength" or hardness of a gel is measured by compressing the gel to a chosen extent (such as 20%) and at a chosen rate and recording the applied force as a function of, e.g., time. The gel strength [which is normally given in Newtons per square meter ($N/m^2$)] is then determined as the peak force on the force-time curve.

Phenolic Polymers

As already briefly indicated above, very suitable types of phenolic polymers for use in the method of the invention are phenolic polysaccharides as defined herein. Phenolic polysaccharides are particularly well suited when the product formed according to the method is to be employed, for example, in the manufacture of a foodstuff for human and/or animal ingestion, as or in the manufacture of a medicinal, therapeutic or other product for ingestion by, or external application to, humans or animals.

Other very interesting classes of phenolic polymers in the context of the process of, and fields of applicability of, the present invention include peptides (polypeptides) and proteins having phenolic substituents. Naturally occurring and synthetic (poly)peptides and proteins having phenolic substituents include those with one or more tyrosine residues in the amino acid sequence.

As also indicated above, a number of readily available polysaccharide-based polymers of natural origin (predominantly plant origin) contain substituents derived from cinnamic or benzoic acid, and these substances have proved well suited as starting materials in connection with the formation of gels by the method of the invention. Moreover, as a consequence of their ready biological renewability and degradability such naturally occurring phenolic polymers are highly environmentally friendly.

Some particularly interesting classes of such substances include the following:

Arabinoxylans:

Arabinoxylans containing phenolic substituents derived from cinnamic acid [e.g. derived from ferulic acid (vide supra)] are obtainable from cereals, and they represent one class of useful phenolic polysaccharides. Arabinoxylans contain a backbone of β-1,4-linked xylose units with arabinose (α-linked arabinofuranose) side-branches. The phenolic substituents present in the cereal-derived materials are attached by ester linkages to arabinose groups, e.g. as ferulyl (often denoted feruloyl) groups, i.e. 4-hydroxy-3-methoxycinnamyl groups. The arabinoxylans found in the endosperm of cereals have an arabinose:xylose ratio of about 0.6:1 and are susceptible to xylanase degradation.

Heteroxylans:

Certain types of bran (e.g. wheat bran and maize bran) contain phenolic heteroxylans which are far more branched than arabinoxylans and which may—in addition to arabinose—contain galactose and glucuronic acid units in the side-branches [see, e.g., J. -M. Brillourt and J. -P. Joseleau in *Carbohydr. Res.* 159 (1987) 109–126, and J. -M. Brillourt et al. in *J. Agricultur. Food Chem.* 30 (1982) 21–27]. These heteroxylans are partially resistant to xylanase degradation, and a xylanase-containing enzyme preparation may therefore be used in the purification of these heteroxylans. Heteroxylans having phenolic substituents based on cinnamic acid ester groups can be isolated from the bran using mild alkaline extraction, since the ester linkages via which the substituents are attached are relatively alkali-stable.

Pectins:

Pectins obtainable from members of the plant family Chenopodiaceae (which includes beets, spinach and mangelwurzels) contain phenolic substituents derived from cinnamic acid. Pectins are made up of "smooth" regions, based on linear homogalacturonan, and "hairy" (ramified) regions, based on a rhamnogalacturonan backbone with side-branches of varying length.

The linear homogalacturonan part of pectins is based on chains of 1,4-linked α-D-galacturonic acid, and this polygalacturonic acid is methoxylated to varying degrees—depending on the plant species in question—and may (as in e.g. sugar beet pectin) further be partially acetylated. Rhamnogalacturonans are polysaccharides with more or less regularly alternating rhamnose and galacturonic acid residues in the backbone. The rhamnogalacturonan backbone in the hairy regions of pectins have acetyl groups on the galacturonic acid residues (cf. H. A. Schols in *Carbohydr. Res.* 206 (1990) 117–129); the side-branches include oligo- and polysaccharides such as arabinan and arabinogalactan, which are linked to the rhamnose in the rhamnogalacturonan backbone.

Sugar beet pectin is especially rich in arabinan. Arabinan contains β-1,5-linked arabinose in the backbone with α-(1->3)-or α-(1->2)-linked arabinose residues, whereas arabinogalactan contains β-1,4-linked galactose in the backbone, with α-(1->3) or α-(1->2) linked arabinose residues. Ferulyl substituents are linked to the arabinose and/or the galactose in the arabinan and arabinogalactan side-branches of the rhamnogalacturonan part. The "ferulic acid" (ferulyl) content in sugar beet pectin depends upon the method of extraction, but is often about 0.6% [cf. F. Guillon and J. -F. Thibault, *Carbohydrate Polymers* 12 (1990) 353–374].

It is known that beet pectin obtained by a process which results in partial removal of the arabinose residues which are present in beet pectin in the form in which it occurs in, e.g., beet pulp may exhibit improved gelling properties. Thus, e.g., procedures involving a mild acid treatment and/or a treatment with an α-arabinofuranosidase will improve the gelling properties of the pectin [F. Guillon and J. -F. Thibault (vide supra)]. For the purposes of the present invention, "mild acid treatment" involves treating the pectin with 0.1M trifluoroacetic acid at 25° C. for 8 hours, 24 hours and 72 hours, or with 0.05M trifluoroacetic acid at 100° C. in a sealed tube for 1 to 12 hours.

Pectic materials (i.e. pectins or modified pectins) of the above-mentioned types—notably sugar beet pectins—are among the preferred types of phenolic polymers in the context of the invention.

The phenolic-substituted cinnamic acid ester linkages can be hydrolysed by ferulic acid esterases. Enzymes used in the purification of polysaccharides containing substituents of the cinnamic acid type should therefore be essentially free from ferulic acid esterase activity with specificity towards ferulic acid esters of the polysaccharide in question. Under conditions of low water activity, ferulic acid esterase will catalyse the formation of new ester linkages to carbohydrates, and can therefore be used to increase the content of ester residues of the phenolic cinnamic acid ester type (e.g. ferulyl residues) in cereal arabinoxylan and pectin from beet (or other members of the Chenopodiaceae) and thereby their gelling properties.

Polysaccharides (and other types of polymers) which do not contain phenolic residues useful for achieving gelation can be derivatized in order to render them gellable. Under conditions of low water activity, ferulic acid esterases can be used to attach groups of the cinnamic acid ester type (e.g. ferulic acid ester groups) to polymers such as pectin, arabinan, galactan, cellulose derivatives (e.g. hydroxyethylcellulose or carboxymethylcellulose), galactomannans (e.g. guar gum, hydroxypropyl-guar gum or locust bean gum), beta-glucans, xyloglucans, starch, derivatized starch, bacterial gums (e.g. xanthan), algal gums (e.g. alginate or carrageenan), other polysaccharides or other polymers with hydroxyl groups.

Ester linkages to phenolic cinnamic acids (or other phenolic carboxylic acids) may also be synthesized by non-enzymatic methods known in the art. Polymers which contain acid groups, such as pectin and carboxymethylcellulose, can be esterified with polyhydric phenolic substances, e.g. ferulic alcohol, sinapyl alcohol or lignin derivatives, in order to obtain a phenolic polymer with the ability to undergo oxidative gelation.

As already indicated to some extent, particularly interesting phenolic substituents in the context of the present invention include those comprising one or two methoxy groups in an ortho-position in the aromatic ring relative to the phenolic hydroxy group [as in the case of, e.g., ferulyl (4-hydroxy-3-methoxy-cinnamyl) substituents].

The concentration of phenolic polymer (e.g. phenolic polysaccharide) present in the aqueous medium employed in the process of the invention will normally be in the range of 0.1–10% by weight of the medium, for example in the range of 0.5–5% by weight. Concentrations of phenolic polymer in the range of about 1–5% by weight will often be appropriate.

Enzymes

As already indicated, the preferred enzymes in the context of the present invention are laccases (EC 1.10.3.2), which are oxidases (i.e. enzymes employing molecular oxygen as acceptor) capable of catalyzing oxidation of phenolic groups. Examples of other potentially useful, phenol-oxidizing oxidases in the context of the invention include the catechol oxidases (EC 1.10.3.1). The use of mixtures of different phenol-oxidizing oxidases may also be appropriate in some cases.

Contact of a reaction mixture (containing phenolic polymer and enzyme) with atmospheric air will normally suffice to ensure an adequate supply of oxygen for the oxidation reaction, although forcible aeration of reaction mixtures with air, or possibly even substantially pure oxygen, may be advantageous under certain conditions.

Laccases are obtainable from a variety of microbial sources, notably bacteria and fungi (including filamentous fungi and yeasts), and suitable examples of laccases include those obtainable from strains of Aspergillus, Neurospora (e.g. *N. crassa*), Podospora, Botrytis, Collybia, Fomes, Lentinus, Pleurotus, Trametes [some species/strains of which are known by various names and/or have previously been classified within other genera; e.g. *Trametes villosa=T. pinsitus=Polyporus pinsitis* (also known as *P. pinsitus* or *P. villosus*)=*Coriolus pinsitus*], Polyporus, Rhizoctonia (e.g. *R. solani*), Coprinus (e.g. *C. plicatilis*), Psatyrella, Myceliophthora (e.g. *M. thermophila*), Schytalidium, Phlebia (e.g. *P. radita*; see WO 92/01046), or Coriolus (e.g. *C. hirsutus*; see JP 2-238885).

A preferred laccase in the context of the invention is that obtainable from *Trametes villosa*.

Before adding the enzyme (e.g. a laccase) to a solution containing phenolic starting material(s) (e.g. a phenolic polysaccharide), it will generally be preferable to adjust the pH of the solution to a value equal to, or in the vicinity of, the optimum pH for the enzyme in question.

For laccases, the amount of laccase employed should generally be in the range of 0.01–1000 kLACU per kg of polysaccharide, preferably 0.05–100 kLACU/kg of polysaccharide, and will typically be in the range of 0.1–100 kLACU per kg of polysaccharide (LACU is the unit of laccase activity as defined below; 1 kLACU=1000 LACU).

Determination of Laccase Activity (LACU)

Laccase activity as defined herein is determined on the basis of spectrophotometric measurements of the oxidation of syringaldazin under aerobic conditions. The intensity of the violet colour produced in the oxidation reaction is measured at 530 nm.

The analytical conditions are: 19 $\mu$M syringaldazin, 23.2 mM acetate buffer, pH 5.5, 30° C., reaction time 1 minute.

1 laccase unit (LACU) is the amount of enzyme that catalyses the conversion of 1 $\mu$M of syringaldazin per minute under these conditions.

Applications

As already indicated above, gelled products or products of increased viscosity produced according to the invention have a wide range of applications, e.g. in the food and feed areas, the pharmaceutical and agricultural areas, and the personal care/personal hygiene area.

A particularly interesting and valuable property of certain gel products ("hydrogels") produced according to the invention is their ability when dried or dehydrated to absorb many times their own weight of liquid (more particularly water or an aqueous medium, e.g. a body fluid such as urine or blood) Materials exhibiting such absorption properties are sometimes referred to as "superabsorbent" materials.

Initially, the most important property in connection with superabsorbent materials was regarded as being the total absorption capacity. Subsequently, however, a number of other properties have been recognized as being of great importance. These properties include the following: rate of absorption; ability to resist so-called gel blocking (whereby part of the absorbing material becomes saturated with liquid and prevents access of further liquid to the remaining part of the absorbing material); and absorption under load (AUL; i.e. the ability of a superabsorbent material to absorb liquid when subjected, e.g., to compression or to centrifugal forces.

Certain products obtainable according to the present invention, e.g. gelled products produced from pectic materials such as sugar beet pectin, have been found to very well suited for use as absorbent materials of the above-outlined type, and the present invention encompasses such use. As examples of applications of the liquid-absorption properties of dried or dehydrated gel products obtainable according to the invention may be mentioned their use as an absorbent in disposable nappies or diapers for infants or for persons suffering from incontinence, or in disposable feminine hygiene products (sanitary towels, sanitary napkins, panty protectors, tampons and the like).

Drying or dehydration of gelled products obtainable according to the invention may suitably be achieved, for example, by drying them under vacuum at ambient temperature or at a moderately elevated temperature (e.g. a temperature up to about 40° C.). In some cases a pre-treatment such as washing with a water-miscible organic solvent (e.g. acetone, ethanol or the like) may be of value in reducing the water content of a gel prior to final drying by, for example, vacuum treatment.

The present invention is further illustrated by the following examples, which are not in any way intended to limit the scope of the invention as claimed.

EXAMPLE 1

Gelation of Feruloyl-Arabinoxylan

A gel of Corn Bran Extract (feruloyl-arabinoxylan powder) was produced in the following way:

Demineralised water (198 ml) was heated to 90° C., and Corn Bran Extract (2.00 g; obtainable from GB Gels Ltd, Wales, UK) was added under vigorous stirring. 5 ml aliquots of the resulting solution were then poured (temperature 40° C.) into 10 ml aluminium forms. Laccase [*Trametes villosa* laccase; produced by Novo Nordisk A/S, Bagsvaerd, Denmark] was added at three different concentration levels: 0.18 LACU/g Corn Bran Extract, 1.8 LACU/g Corn Bran Extract and 18 LACU/g Corn Bran Extract. A control was also prepared, containing 18.0 LACU of inactivated laccase (inactivated by heating at 85° C. for 15 min) per g of Corn Bran Extract. The aluminium sample forms were covered with a lid and left to stand at room temperature.

The hardness of the various gelled samples was measured the following day by Texture Analysis (vide supra), using an SMS Texture Analyzer TA-XT2 (Stable Micro Systems; XT.RA Dimensions, Operating Manual version 37) with a flat compression cylinder of diameter 20 mm.

The measurement conditions were as follows:
% gel deformation (compression): 20%
Rate of deformation (compression): 2 mm/sec
pH of all samples remained unadjusted at 4.9.

The results obtained are given below (average of four measurements). It should be noted that for simplicity, the peak force for each gel is given here in Newtons (N) rather than $N/m^2$, since the various gel samples all had the same cross-sectional area:

| Ratio of laccase to Corn Bran Extract (LACU/g) | Force (N) |
| --- | --- |
| 0.18 | 0.20 |
| 1.80 | 0.44 |
| 18.0 | 0.71 |

EXAMPLE 2

Gelation of Sugar Beet Pectin

Solutions containing 1%, 2% and 3% by weight (w/w), respectively, of pectic material were prepared by dissolving different amounts of sugar beet pectin [cf. F. Guillon and J.-F. Thibault, *Carbohydr. Polym.* 12 (1990) 353–374 (vide supra); α-arabinofuranosidase suitable for this purpose is obtainable from Megazyme, Australia] in aqueous 0.05 M $NaH_2PO_4$ buffer solution, adjusting the pH of each solution to 5.5 by addition of 0.5 M NaOH, and adjusting the final pectin concentration of each solution by addition of distilled water. The solutions were then thermostatted in a water bath at 30° C.

To samples of each pectin solution were added different amounts of laccase preparation [*Trametes villosa* laccase; produced by Novo Nordisk A/S, Bagsvaerd, Denmark] containing 275 LACU/g of laccase preparation. The resulting solutions were then stirred mechanically until gelation occurred. The gels were then thermostatted at 30° C. overnight.

Each gel sample was washed by allowing it to stand in 300 ml of distilled water for 1–2 hours. Water was removed by filtration on a steel mesh filter. The individual gels were rinsed thoroughly with copious amounts of water, washed with acetone (300 ml) and dried in a vacuum drying oven at 30° C. overnight. The thus-dried products were cut into pieces and comminuted in a small laboratory mill (Retsch Ultra Centrifugal Mill ZM 1000, with ring sieve 6.0)

The following table shows the various combinations of pectin concentration and laccase concentration employed in the preparation of each gel:

| Gel No. | Pectin concn. (% w/w) | Laccase concn. (LACU/g pectin) |
| --- | --- | --- |
| 1 | 1 | 1.0 |
| 2 | 1 | 7.5 |
| 3 | 2 | 0.5 |
| 4 | 2 | 1.0 |
| 5 | 2 | 7.5 |
| 6 | 2 | 15 |
| 7 | 2 | 30 |
| 8 | 3 | 1.0 |
| 9 | 3 | 7.5 |
| 10 | 3 | 15 |
| 11 | 3 | 30 |

The Free Swelling Capacity (FSC; i.e. the liquid uptake per gram of dried gel) and the Retention Capacity (RC; i.e. the liquid retention per gram of dried gel) of each of the dried gels was determined as follows:

FSC:

A 0.2 g sample of comminuted dried gel was placed in a fine-mesh nylon "teabag" (3.5×6 cm). The closed "teabag" was then immersed for 1 hour in an aqueous solution simulating human urine, and having the following composition:

60 mM KCl, 130 mM NaCl, 3.5 mM $MgCl_2.6H_2O$, 2.0 mM $CaCl_2.2H_2O$, 300 mM urea, surface tension adjusted to 60 dynes/cm by addition of Triton™ X-100 (Rohm & Haas) [surface tension measurements made with a CAHN Dynamic Contact Angle Analyzer (Cahn Instrument Inc.) using the Wilhelmy plate technique].

The soaked "teabag" with contents was allowed to drip-dry for 2 minutes. The FSC for the gel in question was calculated by dividing the weight (in grams) of liquid absorbed by the gel sample in the teabag by the initial weight (0.2 g) of the dry gel sample.

RC:

The drip-dried "teabag" was centrifuged (WIFUG laboratory centrifuge 500 E) at 327×g for 10 minutes. RC for the gel in question was calculated by dividing the weight (in grams) of absorbed liquid remaining in the teabag after centrifugation by initial weight (0.2 g) of the dry gel sample.

The results of the FSC and RC measurements for the various gels are shown in the table below. The corresponding data for a sample of ungelled sugar beet pectin are included for comparison:

| Dried Gel No. | FSC (g/g) | RC (g/g) |
|---|---|---|
| 1 | 12 | 6 |
| 2 | 17 | 10 |
| 3 | 19 | 11 |
| 4 | 21 | 13 |
| 5 | 20 | 12 |
| 6 | 19 | 11 |
| 7 | 19 | 11 |
| 8 | 20 | 10 |
| 9 | 20 | 11 |
| 10 | 19 | 11 |
| 11 | 18 | 10 |
| Ungelled pectin | 3 | ** |

**: the sample passed through the nylon mesh of the "teabag"

It is apparent from the above that dried gels prepared from phenolic polysaccharides, in this case sugar beet pectin, in the manner according to the invention can exhibit excellent liquid-absorption and liquid-retention properties.

What is claimed is:

1. A method for causing gelling or increase of viscosity of an aqueous medium containing a gellable polymeric material having substituents with phenolic hydroxy groups, the method comprising adding to said aqueous medium an amount of a laccase effective for increasing said viscosity.

2. The method of claim 1, wherein said gellable polymeric material is a polysaccharide having substituents with phenolic hydroxy groups.

3. The method of claim 1, wherein the phenolic substituents are cinnamic acid ester groups.

4. The method of claim 2, wherein the polysaccharide is an arabinoxylan or a material comprising pectin.

5. The method of claim 4, wherein the arabinoxylan is obtainable from a cereal.

6. The method of claim 5, wherein the cereal is wheat or maize.

7. The method of claim 4, wherein the arabinoxylan is extracted from flour or bran.

8. The method of claim 4, wherein the pectic material is from a member of the family Chenopodiaceae.

9. The method of claim 8, wherein the pectic material is from sugar beets.

10. The method of claim 9, wherein the pectic material is extracted from sugar beet pulp.

11. The method of claim 1, wherein the gellable polymeric material cones two or more polysaccharides having phenolic substituents.

12. The method of claim 11, wherein the phenolic substituents are cinnamic acid ester groups.

13. The method of claim 11, wherein the gellable polymeric material comprises an arabinoxylan and a material comprising pectin.

14. The method of claim 13, wherein the arabinoxylan is a cereal arabinoxylan and the pectic material is beet pectin.

15. The method of claim 14, wherein the cereal arabinoxylan is wheat or maize.

16. The method of claim 1, wherein the laccase is derived from a microorganism.

17. The method of claim 16, wherein the microorganism is a fungus.

18. The method of claim 17, wherein the laccase is derived from a member of the genus Trametes or the genus Myceliophthora.

19. The method of claim 18, wherein the laccase is derived from *Trametes villosa* or from *Myceliophthora thermophila*.

20. The method of claim 1, wherein the amount of laccase employed is in the range from 0.01 to 100 kLACU per kg of gellable polymeric material.

21. The method of claim 13, wherein the gelled product is subjected to a drying or dehydration procedure.

* * * * *